(12) United States Patent
Brandon

(10) Patent No.: US 10,441,690 B2
(45) Date of Patent: Oct. 15, 2019

(54) SYSTEMS AND METHODS WOUND DRAINAGE MANAGEMENT

(71) Applicant: Western Connecticut Health Network, Inc., Danbury, CT (US)

(72) Inventor: Theresa Brandon, Brewster, NY (US)

(73) Assignee: Western Connecticut Health Network, Inc., Danbury, CT (US)

( * ) Notice: Subject to any disclaimer, the term of this patent is extended or adjusted under 35 U.S.C. 154(b) by 971 days.

(21) Appl. No.: 14/820,964

(22) Filed: Aug. 7, 2015

(65) Prior Publication Data

US 2016/0038659 A1    Feb. 11, 2016

Related U.S. Application Data

(60) Provisional application No. 62/035,692, filed on Aug. 11, 2014.

(51) Int. Cl.
*A61M 1/00* (2006.01)
*A61B 5/00* (2006.01)

(52) U.S. Cl.
CPC ........ *A61M 1/0019* (2013.01); *A61M 1/0025* (2014.02); *A61M 1/0088* (2013.01); *A61B 5/6802* (2013.01); *A61B 5/6832* (2013.01); *A61B 2505/05* (2013.01); *A61M 1/0005* (2013.01); *A61M 2202/0014* (2013.01); *A61M 2205/3303* (2013.01); *A61M 2205/3389* (2013.01); *A61M 2205/584* (2013.01); *A61M 2209/082* (2013.01); *A61M 2209/088* (2013.01)

(58) Field of Classification Search
CPC . A61M 1/0019; A61M 1/0025; A61M 1/0088
See application file for complete search history.

(56) References Cited

U.S. PATENT DOCUMENTS

| | | | |
|---|---|---|---|
| 2,886,036 A | | 2/1956 | Price |
| 3,585,997 A | * | 6/1971 | Ancerewicz, Jr. .. A61M 16/047 604/327 |
| 3,736,934 A | * | 6/1973 | Hennessy ............... A61F 5/448 604/342 |
| 3,897,780 A | | 8/1975 | Trousil |
| 4,475,908 A | | 10/1984 | Lloyd |
| 4,890,608 A | | 1/1990 | Steer |
| 4,929,245 A | * | 5/1990 | Holtermann ............ A61F 5/448 604/338 |
| 5,074,852 A | | 12/1991 | Castellana et al. |

(Continued)

FOREIGN PATENT DOCUMENTS

CA    1125614    6/1982
WO    WO 1984/003838    10/1984

(Continued)

OTHER PUBLICATIONS

PCT Invitation to Pay Additional Fees issued in International Application No. PCT/US2015/044198, dated Nov. 6, 2015.

(Continued)

*Primary Examiner* — Ariana Zimbouski
(74) *Attorney, Agent, or Firm* — Parker Highlander PLLC

(57) ABSTRACT

Systems and methods for wound drain management. Certain embodiments include an infection indicator and/or a coupling device configured to such that a wound drainage container can rotate in relation to a mounting device.

15 Claims, 4 Drawing Sheets

(56) References Cited

U.S. PATENT DOCUMENTS

| | | | |
|---|---|---|---|
| 5,188,609 | A | 2/1993 | Bayless et al. |
| 5,211,642 | A | 5/1993 | Clendenning |
| 5,330,454 | A | 7/1994 | Klingler et al. |
| 5,989,235 | A | 11/1999 | Quacquarella et al. |
| 6,283,945 | B1 | 9/2001 | Bierman |
| 6,582,410 | B1 * | 6/2003 | Rutman .............. A61F 5/441 604/332 |
| 7,223,256 | B2 | 5/2007 | Bierman |
| 7,819,850 | B2 | 10/2010 | Mullejans et al. |
| 8,343,122 | B2 | 1/2013 | Gorres |
| 2004/0100376 | A1 * | 5/2004 | Lye .............. A61B 5/411 340/539.12 |
| 2009/0216206 | A1 * | 8/2009 | Nishtala .............. A61M 39/10 604/327 |
| 2010/0191197 | A1 | 7/2010 | Braga et al. |
| 2010/0228205 | A1 * | 9/2010 | Hu .............. A61M 1/0037 604/319 |
| 2010/0298789 | A1 * | 11/2010 | Santimaw .............. A61F 5/4405 604/319 |
| 2010/0318071 | A1 | 12/2010 | Wudyka |
| 2011/0275104 | A1 * | 11/2011 | Zimmerle .............. G01N 33/523 435/23 |
| 2012/0310188 | A1 | 12/2012 | Croizat et al. |
| 2013/0226114 | A1 | 8/2013 | Massi et al. |
| 2013/0245585 | A1 | 9/2013 | Letellier |
| 2016/0000378 | A1 * | 1/2016 | Hall .............. A61B 5/0075 702/19 |
| 2017/0130219 | A1 * | 5/2017 | Birnboim .............. C12N 1/06 |

FOREIGN PATENT DOCUMENTS

| | | |
|---|---|---|
| WO | WO 1996/000096 | 1/1996 |
| WO | WO 2008/063160 | 5/2008 |
| WO | WO 2009/047524 | 4/2009 |
| WO | WO 2013/171585 | 11/2013 |

OTHER PUBLICATIONS

"400cc PVC Evacuator Kits," Part No. DYNJWE403, Medline Industries, generated from http://www.medline.com/sku/item/MDPDYNJWE403;ecomsessionid=on6b3rhQugS617UNCXozHA_?skuIndex=S4&question=&flowType=&indexCount=, on Mar. 1, 2016.

"Bile Bags," Part No. 0015860, C.R. Bard, Inc., retrieved from http://www.bardmedical.com/products/bowel-gastric-management/gastric-management/bile-bags/, on Mar. 1, 2016.

"Drainage Bags by C.R. Bard," C.R. Bard, Inc. Part No. 154004, retrieved from http://www.medline.com/sku/item/MDPBRD154004?skuIndex=S9&question=&flowType=&indexCount=, on Mar. 1, 2016.

"Silicone Bulb Evacuators for Closed Wound Drainage," Part No. DYNJWE1305, Medline Industries, generated from website https://www.medline.com/sku/item/MDPDYNJWE1305?skuIndex=S3&question=&flowType=&indexCount=, on Mar. 1, 2016.

"Statlock® Foley Stabilization Device, Tricot Anchor Pad, for 3-Way Catheters," Part No. FOL0105, C.R. Bard, Inc., brochure, 2010.

PCT International Search Report and Written Opinion issued in International Application No. PCT/US2015/044198, dated Feb. 5, 2016.

\* cited by examiner

SYSTEMS AND METHODS WOUND DRAINAGE MANAGEMENT

CROSS-REFERENCE TO RELATED APPLICATIONS

This application claims priority to U.S. Provisional Patent Application Ser. No. 62/035,692 filed Aug. 11, 2014, the contents of which are incorporated by reference herein.

I. FIELD OF THE INVENTION

Embodiments of the present invention relate to systems, devices and methods for wound drainage management.

II. BACKGROUND INFORMATION

Existing systems and methods of managing wound drainage do not adequately address several issues related to patient comfort and safety. For example, when patients wake up from surgery with the dismal awareness that they have lost something, the surgical patient often pulls in their energy to protect the wound resulting from the human body's instinct to protect itself. For a patient who wakes up with one or several drains coming out of the skin near the incision, this reaction can be intensified. The fear of pulling the drains out or pulling on the skin where the drains are sewn in can be intense. Energy that the patient could use for healing is uselessly wasted on guarding poorly anchored drainage systems.

In addition, the weight of the wound drainage systems as blood and body fluids collect can create other issues. For example, drains are currently often clipped or safety-pinned to the patient's gown, which is typically tied at the neck. This added weight pulls on the patient's neck, shoulders and back increasing both muscle ache and fatigue. In the already compromised patient, this added discomfort is an unneeded stress that can magnify exhaustion.

An additional issue with many existing systems involves emptying the drains themselves and infection control. The current systems available for drainage typically have the patient or caregiver empty the fluids into a specimen cup for measuring and then pour the body fluids into the sink or toilet. These fluids consisting of frank blood, body fluids and often infected fluids from abscessed wounds can expose the patient, caregiver, and the environment to potential toxins. Existing systems do not provide for indication of the level of potential toxins.

Accordingly, existing systems include many shortcomings, not limited to those described above. Improved wound drainage management is therefore desirable for several reasons including increased patient comfort and safety.

SUMMARY OF THE INVENTION

Certain embodiments include a wound drainage system comprising a mounting device configured to couple to a patient, and a wound drainage container configured to couple to the mounting device. In particular embodiments, the wound drainage container comprises a first coupling device, the mounting device comprises a first side and a second side, the first side of the mounting device comprises an adhesive, the second side of the mounting device comprises a second coupling device, and the first coupling device is configured to couple to the second coupling device such that the wound drainage container can rotate in relation to the mounting device when the first and second coupling devices are coupled together.

In some embodiments, the wound drainage container comprises an infection detector, and in specific embodiments the infection detector is a leukocyte esterase indicator. In certain embodiments, the infection detector is located within the wound drainage container, and the infection detector is visible through the wound drainage container. In particular embodiments, the wound drainage container comprises a transparent portion, and the infection detector is visible through the transparent portion of the wound drainage container. In some embodiments, the wound drainage container comprises volume indicators.

In specific embodiments, the first coupling device is a button and the second coupling device is an aperture configured to receive the button, and in certain embodiments, the second coupling device is a button and the first coupling device is an aperture configured to receive the button. In particular embodiments, the first coupling device and the second coupling device form a snap mechanism. In some embodiments, the wound drainage container comprises a first port and a second port.

Specific embodiments include a wound drainage system comprising a wound drainage container and an infection detector, where the infection detector is located within the wound drainage container, and the infection detector is visible through the wound drainage container. In certain embodiments, the wound drainage container comprises a transparent portion; and the infection detector is visible through the transparent portion of the wound drainage container.

Particular embodiments further comprise a first coupling device. Some embodiments further comprise a mounting device comprising a second coupling device, where: the first coupling device is configured to couple to the second coupling device; and the wound drainage container can rotate in relation to the mounting device when the first and second coupling devices are coupled together. In specific embodiments, the mounting device comprises a first side and a second side, the first side of the mounting device comprises an adhesive, and the second side of the mounting device comprises the coupling device. In certain embodiments, the wound drainage container comprises a first port and a second port.

Particular embodiments include a method of securing a wound drainage container, where the method comprises coupling the wound drainage container to a mounting device, and where the wound drainage container can rotate in relation to the mounting device when the wound drainage container and the mounting device are coupled together. In some embodiments of the method, the mounting device comprises an adhesive, and the mounting device is secured to a surface via the adhesive. In particular embodiments of the method, the surface is an epidermis of a patient. In specific embodiments of the method, the wound drainage container comprises an infection detector. In certain embodiments of the method, the infection detector is a leukocyte esterase indicator, and in specific embodiments, the leukocyte esterase indicator is configured to change color when exposed to a fluid with a white blood cell count above a threshold. Some embodiments of the method further comprise viewing the leukocyte esterase indicator to determine if the leukocyte esterase indicator has changed color.

In particular embodiments of the method, the wound drainage container comprises a port. Specific embodiments of the method further comprise coupling tubing to the port, and coupling the tubing to a wound dressing.

Any embodiment discussed with respect to one aspect of the invention applies to other aspects of the invention as well.

The embodiments in the one section of this disclosure are understood to be embodiments of the invention that are applicable to all aspects of the invention, including those in other sections of the disclosure.

The use of the term "or" in the claims is used to mean "and/or" unless explicitly indicated to refer to alternatives only or the alternatives are mutually exclusive, although the disclosure supports a definition that refers to only alternatives and "and/or."

Throughout this application, the term "about" is used to indicate that a value includes the standard deviation of error for the device or method being employed to determine the value.

Following long-standing patent law, the words "a" and "an," when used in conjunction with the word "comprising" in the claims or specification, denotes one or more, unless specifically noted.

The term "coupled" is defined as connected, although not necessarily directly, and not necessarily mechanically; two items that are "coupled" may be unitary with each other. The terms "a" and "an" are defined as one or more unless this disclosure explicitly requires otherwise. The terms "substantially" and "generally" are defined as largely but not necessarily wholly what is specified (and includes what is specified; e.g., substantially 90 degrees includes 90 degrees and generally parallel includes parallel), as understood by a person of ordinary skill in the art. In any disclosed embodiment, the terms "substantially," "approximately," and "about" may be substituted with "within [a percentage] of" what is specified, where the percentage includes 0.1, 1, 5, and 10 percent.

The terms "comprise" (and any form of comprise, such as "comprises" and "comprising"), "have" (and any form of have, such as "has" and "having"), "include" (and any form of include, such as "includes" and "including") and "contain" (and any form of contain, such as "contains" and "containing") are open-ended linking verbs. As a result, an apparatus that "comprises," "has," "includes" or "contains" one or more elements possesses those one or more elements, but is not limited to possessing only those elements. Likewise, a method that "comprises," "has," "includes" or "contains" one or more steps possesses those one or more steps, but is not limited to possessing only those one or more steps.

Further, a wound drain management system, or a component of such a system, that is configured in a certain way is configured in at least that way, but it can also be configured in other ways than those specifically described.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

BRIEF DESCRIPTION OF THE DRAWINGS

These and other objects, features, and advantages of the invention will become apparent from the detailed description below and the accompanying drawings.

DETAILED DESCRIPTION OF THE INVENTION

Figure 1:
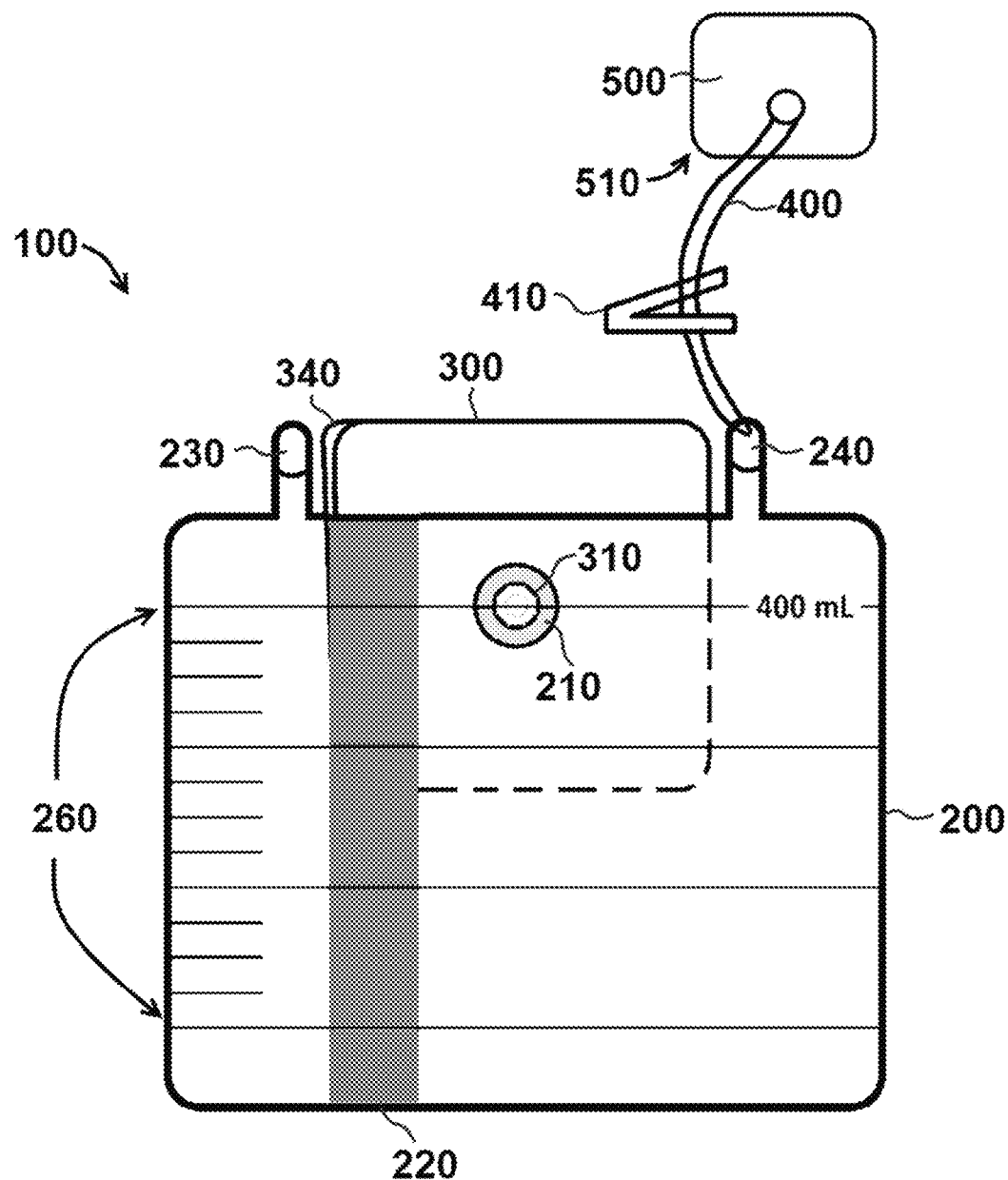
FIG. 1 is a front view of an exemplary embodiment of a wound drainage system coupled to a wound dressing via tubing.
Figure 2:
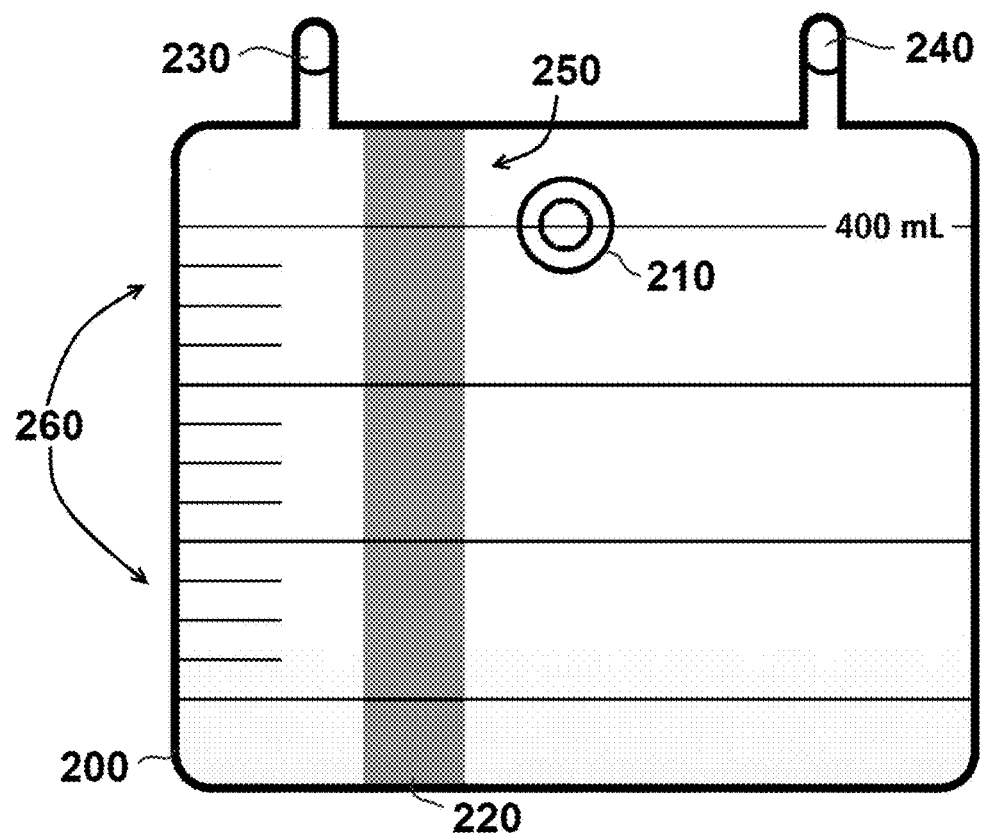
FIG. 2 is a front view of the wound drainage container of the embodiment of FIG. 1.
Figure 3:
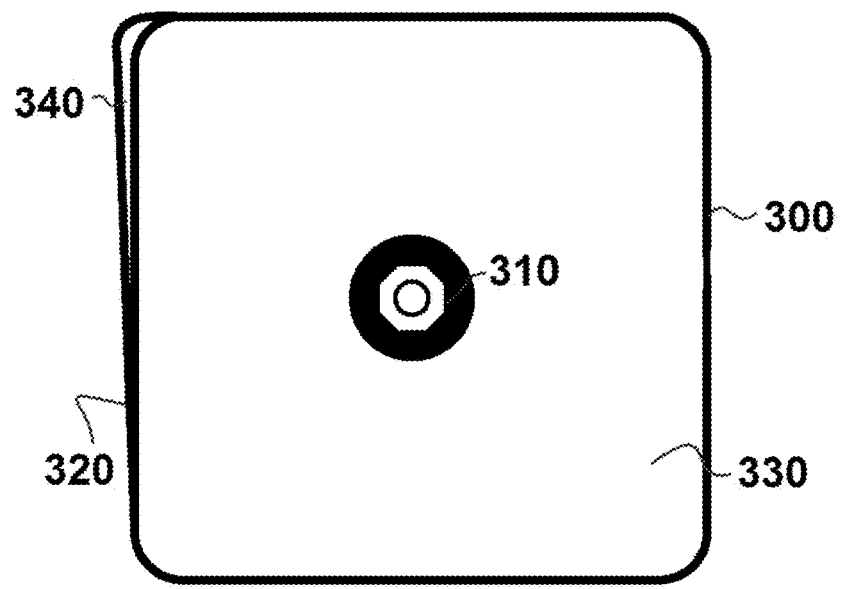
FIG. 3 is a front view of a mounting device of the embodiment of FIG. 1.

Referring initially to FIGS. 1-3, a wound drainage system 100 comprises a wound drainage container 200 and a mounting device 300. In exemplary embodiments, wound drainage container 200 comprises a first coupling device 210 that is configured to couple to a second coupling device 310 of mounting device 300. In the embodiment shown, wound drainage container 200 also comprises an infection detector 220. Wound drainage container 200 may also comprise a first port 230 and a second port 240 configured as an inlet to receive fluids via tubing 400 from a wound site 510 and/or serve as an outlet to drain fluids from wound drainage container 200. In exemplary embodiments, first port 230 and second port 240 can be sealed with a cap or other suitable means when not being used to transfer fluid into or out of wound drainage container 200.

In particular embodiments, mounting device 300 comprises a first side 320 and a second side 330. In the embodiment shown, second side 330 comprises second coupling device 310, while first side 320 comprises an adhesive 340. During use, adhesive 340 can be placed on a surface of a patient (or any person utilizing wound drainage system 100) such that mounting device 300 is securely mounted to the surface. In some embodiments, adhesive 340 may be applied directly to the skin (e.g. epidermis) of the person, while in other embodiments the adhesive may be applied to another surface secured to the person, including for example, a belt, shoulder strap, etc. In still other embodiments, mounting device 300 may be secured to the person without the use of an adhesive. For example, first side 320 may comprise one or more additional coupling devices configured to couple to a support device (e.g. a belt, shoulder strap, etc.)

Figure 4:
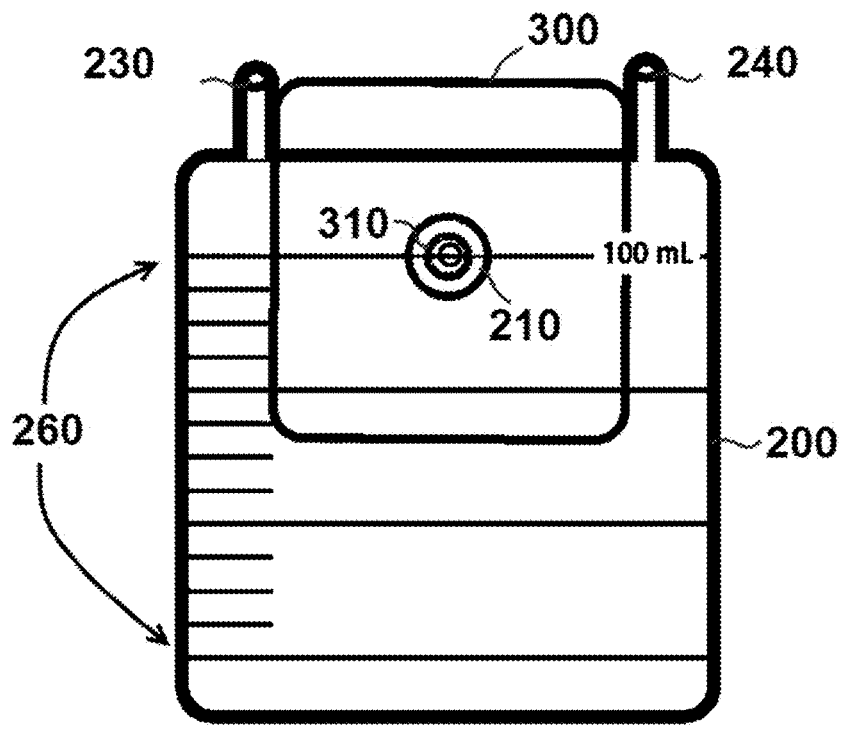
FIG. 4. is a front view of the wound drainage container of FIG. 2 coupled to the mounting device of FIG. 3 in a first position.
Figure 5:
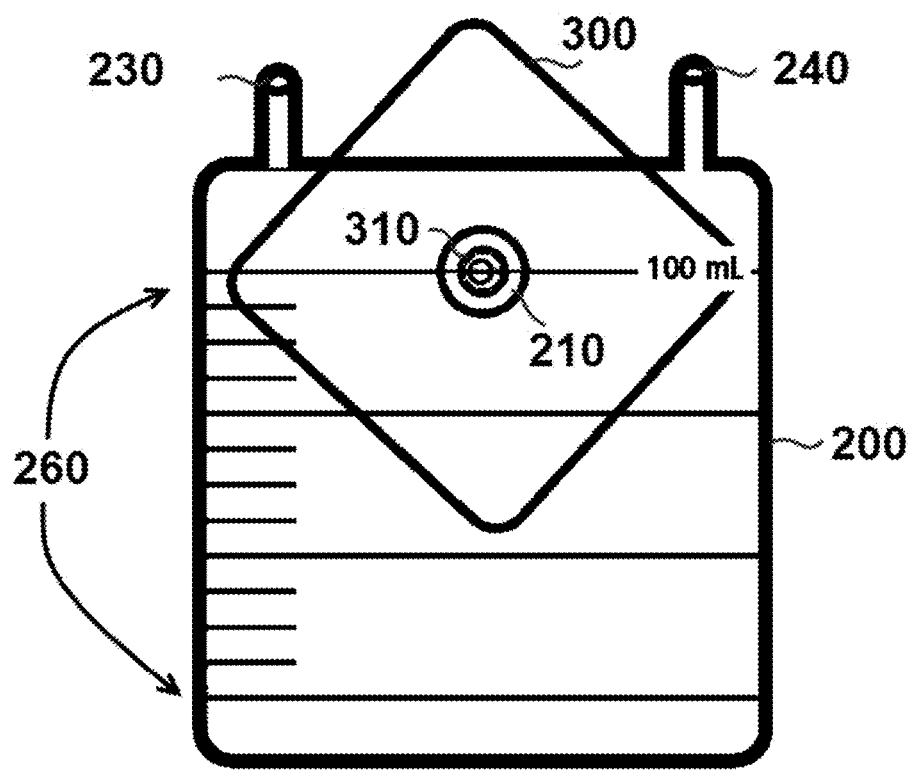
FIG. 5 is a front view of the wound drainage container of FIG. 2 coupled to the mounting device of FIG. 3 in a second position.

Referring now to FIGS. 4-5, exemplary embodiments of wound drainage system 100 are shown in two different positions. It is understood that not all features of wound drainage system 100 are shown or labeled in FIGS. 4-5 for purposes of clarity. For example, infection detector 220 is not shown in FIGS. 4-5 so that the relationship between mounting device 300 and wound drainage container 200 can be more clearly shown. It is also noted that wound drainage container 200 may be configured in different sizes or volumes. For example, the embodiment shown in FIGS. 4-5 comprises a 100 mL capacity, while the embodiment shown in FIGS. 1 and 2 comprises a 400 mL capacity. It is understood that the capacities shown in the figures are merely exemplary, and that other embodiments may comprise different volumes than those shown.

In particular embodiments, first coupling device and second coupling device 310 are configured to form a swivel or pivot mechanism that allow wound drainage container 200 to rotate in relation to mounting device 300 when first and second coupling devices 210 and 310 are coupled together. For example, second coupling device 310 may be configured as a button and first coupling device 210 may be configured as an aperture that receives first coupling device 210 (or vice versa). In other embodiments, first and second coupling devices 210 and 310 may be configured as a snap mechanism that allows rotation when the devices are coupled to each other.

As shown in FIG. 4, wound drainage container 200 and mounting device 300 are shown in a first position. Specifically, the sides of mounting device 300 and wound drainage container 200 are both shown in a vertical orientation. This position may result, for example, when the person using wound drainage system 100 is standing in an upright position. As shown in FIG. 5, the orientation of mounting device 300 with respect to wound drainage container 200 has changed from that of FIG. 4. Specifically, mounting device 300 has rotated approximately 45 degrees, while wound drainage container 200 has maintained the vertical orientation previously shown in FIG. 4. As previously described, first and second coupling devices 210 and 310 allow wound drainage container 200 and mounting device 300 to swivel or rotate with respect to each other.

This configuration can provide for increased patient comfort by allowing the patient to change position while maintaining a consistent position of wound drainage container 200 (and any clamps 410 or tubing 400 coupled to ports 230 and 240). For example, if wound drainage container 200 was fixed to mounting device 300 without the ability to rotate or swivel, any movement of mounting device 300 would also result in movement of wound drainage container 200. As wound drainage container 200 receives fluid from wound site 510 via a wound dressing 500 (as shown in FIG. 1), the weight of wound drainage container 200 increases. Without the ability to pivot or rotate, increased weight of wound drainage container 200 would lead to increased forces exerted mounting device 300 (and consequently, the person using wound drainage system 100) as the person moved. The weight of the fluid in a non-rotational drainage container would exert a torque on the mounting device because the fluid is located some distance from the location where the mounting device is secured to the person. Accordingly, the ability of wound drainage container 200 to rotate with respect to mounting device 300 significantly reduces or eliminates torque exerted on the mounting location resulting from the movement of the patient.

In the embodiment shown, wound drainage container 200 comprises infection detector 220, which can be used to detect an infection in a wound that drains to wound drainage container 200. In specific embodiments, infection detector 220 is a leukocyte esterase indicator. In particular embodiments, infection detector 220 is located within wound drainage container 200 and is visible through wound drainage container 200. In specific embodiments, wound drainage container 200 comprises a transparent portion 250 through which infection detector 220 is visible.

In certain embodiments, transparent portion 250 may include only a portion of wound drainage container 200 (e.g. an outer side, or a portion of the outer side, of wound drainage container 200 that is opposed to the side with coupling device 210). In other embodiments, transparent portion 250 may include the substantially all of wound drainage container 200 (e.g. wound drainage container 200 may be formed from a transparent material). It is understood that as used herein the term "transparent" includes materials that allow a person to detect a color change of a leukocyte esterase indicator strip viewed on the other side of the material. The term "transparent" as used herein does not require a material be able to transmit all light from one side of the material to the other side.

In particular embodiments, infection detector 220 is configured as a leukocyte esterase indicator strip and can be monitored for a color change to determine if a fluid contained within wound drainage container 200 (e.g. a fluid drained from a wound) comprises a white blood cell count that is above a particular threshold. An elevated white blood cell count can be an indication that the wound from which fluid is being drained is infected. The ability to monitor the white blood cell count of fluid being drained from the wound into wound drainage container 200 can allow for early detection of infection and provide a health care professional the opportunity to address the issue before further complications may arise.

In the embodiment shown, wound drainage container 200 also comprises features to facilitate removal and replacement of the container. For example, the ability of wound drainage container 200 to rotate or swivel with respect to mounting device 300 can accommodate the changing positions of the patient from supine to upright. This can allow the patient to be placed in a position that is convenient to access wound drainage container 200 for removal and, if necessary, replacement.

In addition to the features cited above, the embodiment of wound drainage container 200 shown in the figures also comprises a series of volume indicators 260. This can provide a user or medical personnel and indication of the volume of fluid contained within wound drainage container 200 and allow for replacement of the container if necessary. Exemplary embodiments of wound drainage container 200 may be configured to retain different volumes of fluid. For example certain embodiments may be configured to retain 100 mL, 200 mL, 300 mL, 400 mL, 500 mL or more.

In addition, volume indicators 260 can allow a user or medical professional to document the amount of fluid in the container without having to transfer the fluid to a separate container for measurement. This can allow the user or medical personnel to document the wound drainage (e.g. for historical or tracking purposes) without having to be exposed to the fluid during transfer. A clamp 410 (shown in FIG. 1) can be placed on tubing 400 to prevent fluid from exiting wound drainage container 200. In addition, first coupling device 210 and second coupling device 310 can be de-coupled to allow wound drainage container 200 to be separated from mounting device 300. Tubing 400 can be removed and ports 230 and/or 240 can then be capped to prevent fluid from leaking from wound drainage container 200. If desired, a replacement wound drainage container 200 can be coupled to tubing 400 (e.g. via port 230 or 240) and first coupling device 210 coupled to second coupling device 310 to secure wound drainage container 200 to mounting device 300.

It should be understood that the present systems, devices and methods are not intended to be limited to the particular forms disclosed. Rather, they are to cover all modifications, equivalents, and alternatives falling within the scope of the claims.

The above specification and examples provide a complete description of the structure and use of an exemplary embodiment. Although certain embodiments have been described above with a certain degree of particularity, or with reference to one or more individual embodiments, those skilled in the art could make numerous alterations to the disclosed embodiments without departing from the scope of this invention. As such, the illustrative embodiment of the present devices is not intended to be limited to the particular forms disclosed. Rather, they include all modifications and alternatives falling within the scope of the claims, and embodiments other than the one shown may include some or all of the features of the depicted embodiment. Further, where appropriate, aspects of any of the examples described above may be combined with aspects of any of the other examples described to form further examples having comparable or different properties and addressing the same or different problems. Similarly, it will be understood that the benefits and advantages described above may relate to one embodiment or may relate to several embodiments.

The claims are not to be interpreted as including means-plus- or step-plus-function limitations, unless such a limitation is explicitly recited in a given claim using the phrase(s) "means for" or "step for," respectively.

REFERENCES

The following references, to the extent that they provide exemplary procedural or other details supplementary to those set forth herein, are specifically incorporated herein by reference.

U.S. Pat. No. 2,886,036
U.S. Pat. No. 3,897,780
U.S. Pat. No. 4,475,908
U.S. Pat. No. 4,890,608
U.S. Pat. No. 5,074,852
U.S. Pat. No. 5,188,609
U.S. Pat. No. 5,211,642
U.S. Pat. No. 5,330,454
U.S. Pat. No. 5,989,235
U.S. Pat. No. 6,283,945
U.S. Pat. No. 7,223,256
U.S. Pat. No. 7,819,850
U.S. Pat. No. 8,343,122
U.S. Patent Publication 20130226114
U.S. Patent Publication 20130245585
PCT Patent Publication WO1996000096
PCT Patent Publication WO2008063160
Canadian Patent 1125614

What is claimed is:

1. A wound drainage system comprising:
a mounting device configured to couple to a patient;
a wound drainage container configured to couple to the mounting device, wherein:
the wound drainage container comprises an infection detector;
the wound drainage container comprises a first coupling device;
the mounting device comprises a first side and a second side;
the first side of the mounting device comprises an adhesive;
the second side of the mounting device comprises a second coupling device;
the first coupling device is configured to couple to the second coupling device such that the wound drainage container can rotate in relation to the mounting device when the first and second coupling devices are coupled together; and
a wound dressing; and
tubing, wherein the wound dressing is coupled to the wound drainage container via the tubing.

2. The wound drainage system of claim 1 wherein the infection detector is a leukocyte esterase indicator.

3. The wound drainage system of claim 1 wherein:
the infection detector is located within the wound drainage container; and
the infection detector is visible through the wound drainage container.

4. The wound drainage system of claim 3 wherein:
the wound drainage container comprises a transparent portion; and
the infection detector is visible through the transparent portion of the wound drainage container.

5. The wound drainage system of claim 1 wherein the wound drainage container comprises volume indicators.

6. The wound drainage system of claim 1 wherein the first coupling device is a button and the second coupling device is an aperture configured to receive the button.

7. The wound drainage system of claim 1 wherein the second coupling device is a button and the first coupling device is an aperture configured to receive the button.

8. The wound drainage system of claim 1 wherein the first coupling device and the second coupling device form a snap mechanism.

9. The wound drainage system of claim 3 wherein the wound drainage container comprises a first port and a second port.

10. A method of securing a wound drainage container, the method comprising:
coupling the wound drainage container to a mounting device, wherein:
the wound drainage container can rotate in relation to the mounting device when the wound drainage container and the mounting device are coupled together; and
the wound drainage container comprises a port;
the wound drainage container comprises an infection detector;
coupling tubing to the port;
coupling the tubing to a wound dressing.

11. The method of claim 10 wherein:
the mounting device comprises an adhesive; and
the mounting device is secured to a surface via the adhesive.

12. The method of claim 11 wherein the surface is an epidermis of a patient.

13. The method of claim 10 wherein the infection detector is a leukocyte esterase indicator.

14. The method of claim 13 wherein the leukocyte esterase indicator is configured to change color when exposed to a fluid with a white blood cell count above a threshold.

15. The method of claim 14 further comprising viewing the leukocyte esterase indicator to determine if the leukocyte esterase indicator has changed color.

* * * * *